United States Patent
Chiu et al.

(10) Patent No.: US 11,501,510 B2
(45) Date of Patent: Nov. 15, 2022

(54) THERMAL IMAGE POSITIONING METHOD AND SYSTEM THEREOF

(71) Applicant: Wistron Corporation, New Taipei (TW)

(72) Inventors: Chih-Hao Chiu, New Taipei (TW); Hsiu-Mei Lin, New Taipei (TW); Kuo-Hsien Lu, New Taipei (TW)

(73) Assignee: Wistron Corporation, New Taipei (TW)

( * ) Notice: Subject to any disclaimer, the term of this patent is extended or adjusted under 35 U.S.C. 154(b) by 0 days.

(21) Appl. No.: 17/322,890

(22) Filed: May 17, 2021

(65) Prior Publication Data

US 2022/0269894 A1     Aug. 25, 2022

(30) Foreign Application Priority Data

Feb. 20, 2021   (TW) ................... 110105909

(51) Int. Cl.
*G06V 10/22* (2022.01)
*A61B 5/01* (2006.01)
*H04N 5/33* (2006.01)

(52) U.S. Cl.
CPC ............. *G06V 10/22* (2022.01); *A61B 5/015* (2013.01); *H04N 5/33* (2013.01); *G06T 2207/10048* (2013.01)

(58) Field of Classification Search
None
See application file for complete search history.

(56) References Cited

U.S. PATENT DOCUMENTS

| | | | |
|---|---|---|---|
| 8,136,984 B1 * | 3/2012 | Heinke | G01J 5/025 374/170 |
| 10,109,051 B1 * | 10/2018 | Natesh | G06V 10/56 |
| 10,452,922 B2 * | 10/2019 | Herrero Molina | G08B 13/19613 |
| 10,579,897 B2 * | 3/2020 | Redmon | G06V 10/449 |
| 10,764,514 B1 * | 9/2020 | Hoevenaar | G01J 5/025 |
| 11,282,180 B1 * | 3/2022 | Saxena | G06K 9/6256 |
| 2008/0077019 A1 * | 3/2008 | Xiao | A61B 5/015 600/474 |
| 2011/0243409 A1 * | 10/2011 | Naimi | G06T 7/11 382/128 |

(Continued)

FOREIGN PATENT DOCUMENTS

| | | |
|---|---|---|
| CN | 109691989 A | 4/2019 |
| CN | 110411570 B | 8/2020 |

(Continued)

*Primary Examiner* — Stefan Gadomski
(74) *Attorney, Agent, or Firm* — Winston Hsu (57) ABSTRACT

A thermal image positioning method for determining a heat source location of the thermal image is disclosed. The thermal image positioning method includes obtaining a temperature array corresponding to the thermal image and determining a region of interest (ROI) of the temperature array. The thermal image positioning method further includes determining an ROI center reference point of the ROI, determining a plurality of corner points corresponding to the ROI, and determining the heat source location according to at least one of the plurality of corner points. A thermal image positioning system is also disclosed herein.

19 Claims, 6 Drawing Sheets

(56) References Cited

U.S. PATENT DOCUMENTS

| | | | | |
|---|---|---|---|---|
| 2013/0343423 | A1* | 12/2013 | Hosoi | G01K 7/02 374/102 |
| 2014/0010263 | A1* | 1/2014 | Hosoi | G01J 5/12 374/137 |
| 2015/0156431 | A1* | 6/2015 | Nagata | H01L 27/14605 348/340 |
| 2015/0169169 | A1* | 6/2015 | Andersson | G06F 3/0488 715/765 |
| 2016/0063303 | A1* | 3/2016 | Cheung | G06V 40/193 382/103 |
| 2016/0278641 | A1* | 9/2016 | Venkataramani | A61B 5/015 |
| 2017/0088098 | A1* | 3/2017 | Frank | B60H 1/00778 |
| 2018/0046872 | A1* | 2/2018 | Diamond | G16H 40/63 |
| 2018/0110416 | A1* | 4/2018 | Masuda | A61B 5/0077 |
| 2018/0234628 | A1* | 8/2018 | Kobayashi | G01J 1/44 |
| 2018/0239784 | A1* | 8/2018 | Solli | G06K 9/6255 |
| 2018/0284671 | A1* | 10/2018 | Fuse | G03G 15/5004 |
| 2019/0286932 | A1* | 9/2019 | Du | G06V 20/00 |
| 2019/0308372 | A1* | 10/2019 | Fernandez Aymerich | B28B 1/001 |
| 2019/0347501 | A1* | 11/2019 | Kim | G06F 3/011 |
| 2019/0371134 | A1* | 12/2019 | Chen | G06V 10/40 |
| 2020/0094414 | A1* | 3/2020 | Xi | G06V 10/22 |
| 2020/0146557 | A1* | 5/2020 | Cheung | G06V 20/53 |
| 2020/0195854 | A1* | 6/2020 | Winzell | H04N 5/33 |
| 2020/0242790 | A1* | 7/2020 | Addison | A61B 5/1128 |
| 2020/0390337 | A1* | 12/2020 | Frank | G01J 5/0265 |
| 2021/0082564 | A1* | 3/2021 | Colachis | A61B 5/1128 |
| 2021/0216767 | A1* | 7/2021 | Yu | B25J 13/08 |
| 2021/0259654 | A1* | 8/2021 | Yao | G06N 3/08 |
| 2021/0263525 | A1* | 8/2021 | Das | G06T 7/246 |
| 2021/0302235 | A1* | 9/2021 | Fox | G01J 5/52 |
| 2021/0302238 | A1* | 9/2021 | Beall | G01J 5/10 |
| 2021/0397819 | A1* | 12/2021 | Park | G06V 10/454 |
| 2022/0015644 | A1* | 1/2022 | Markov | A61B 5/7203 |
| 2022/0054019 | A1* | 2/2022 | Tang | G06V 10/143 |
| 2022/0090489 | A1* | 3/2022 | Al-Hudaifah | H04N 5/33 |
| 2022/0192507 | A1* | 6/2022 | Lin | G06V 40/103 |
| 2022/0198657 | A1* | 6/2022 | Hall | G06N 3/08 |

FOREIGN PATENT DOCUMENTS

| | | |
|---|---|---|
| KR | 10-1729327 B1 | 4/2017 |
| TW | M601819 | 9/2020 |
| TW | M602631 | 10/2020 |

* cited by examiner

| | | | | | | | | |
|---|---|---|---|---|---|---|---|---|
| -43.9 | -44.7 | -44.7 | -44.7 | 35.7 | 35.7 | 35.7 | 35.7 | 35.8 |
| -43.9 | -45 | -44.5 | -44.2 | 36.2 | 36.2 | 36.2 | 36.2 | 35.8 |
| -43.9 | -43.9 | -43.9 | -43.9 | 36.9 | 36.9 | 36.9 | 36.2 | 35.8 |
| 35.9 | 36.8 | 38.5 | 36.9 | 36.9 | 36.9 | 36.9 | 36.2 | 35.8 |
| 35.9 | -39.4 | -39.4 | -39.4 | -39.4 | -39.4 | -39.4 | 36.2 | 35.8 |
| 35.9 | -39.3 | -42 | -43.5 | -45 | -43.6 | -39.3 | 36.2 | 35.8 |
| 35.9 | -40 | -41 | -42.5 | -43.7 | -43 | -39.3 | 36.2 | 35.8 |
| 35.9 | 36.2 | 36.2 | -39 | -39 | -39 | -39.4 | 36.2 | 35.8 |
| 35.9 | 35.9 | 35.9 | 35.9 | 35.9 | 35.9 | 35.9 | 35.9 | 35.8 |

THERMAL IMAGE POSITIONING METHOD AND SYSTEM THEREOF

BACKGROUND OF THE INVENTION

1. Field of the Invention

The present invention relates to a thermal image positioning method and a thermal image positioning system, and more particularly, to a thermal image positioning method and a thermal image positioning system capable of precisely positioning the location of a heat source within the thermal image.

2. Description of the Prior Art

Thermal imaging is widely utilized for detecting temperatures of human bodies in a quick and effective way. Conventional thermal imaging techniques often take a specific temperature threshold as a reference. Assume that a highest temperature point (being higher than the temperature threshold) of a temperature array corresponding to a thermal image of a human body is located at the forehead. This location will be utilized to represent the temperature of the human body.

Under different environments, however, the highest temperature point of the human body might not be located at the forehead; instead, the highest temperature point may be located at the nose, mouth or neck. In practice, since the conventional thermal imaging device cannot precisely pinpoint the location of the forehead, a solution is to include a camera module which uses visible light to detect and position the face of the human body on the captured thermal image. Since an extra camera module is needed, higher computation resources are required. Therefore, improvements are necessary to the conventional thermal image technique for detecting the temperature of a human body.

SUMMARY OF THE INVENTION

In light of the above problem, the embodiments of the present invention provide a thermal image positioning method and a thermal image positioning system to determine a human body zone and a highest temperature location within a thermal image to precisely position a forehead location of the human body.

An embodiment of the present invention discloses a thermal image positioning method, for determining a heat source location of the thermal image, includes: obtaining a temperature array corresponding to the thermal image, determining a region of interest (ROI) of the temperature array, determining an ROI center reference point of the ROI, determining a plurality of corner points corresponding to the ROI, and determining the heat source location according to at least one of the plurality of corner points.

An embodiment of the present invention discloses a thermal image positioning system, for determining a heat source location of a thermal image, includes a thermal image device and a processing device. The thermal image device is configured to generate a temperature array corresponding to the thermal image. The processing device is coupled to the thermal image device. The processing device is configured to: determine a region of interest (ROI) of the temperature array, determine an ROI center reference point of the ROI, determine a plurality of corner points corresponding to the ROI, and determine the heat source location according to at least one of the plurality of corner points.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
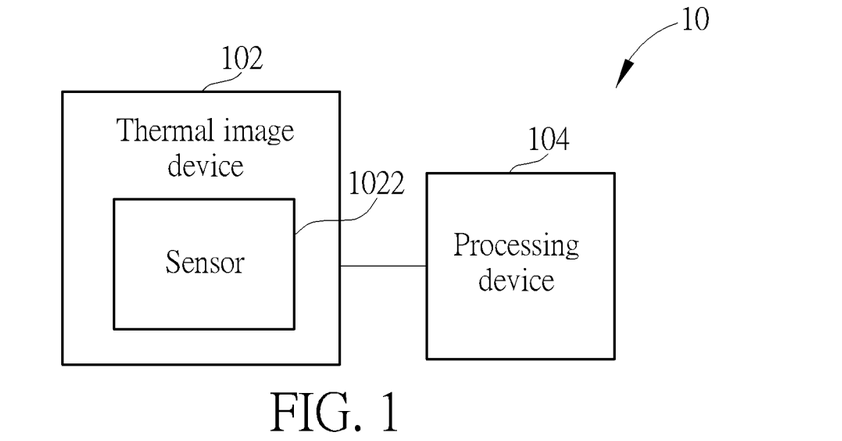
FIG. 1 is a schematic diagram of a thermal image positioning system according to an embodiment of the present invention.

Refer to FIG. 1, which is a schematic diagram of a thermal image positioning system 10 according to an embodiment of the present invention. The thermal image positioning system 10 is configured to determine a heat source location of a thermal image. The thermal image positioning system 10 includes a thermal image device 102 and a processing device 104. The thermal image device 102 includes a sensor 1022, wherein the sensor 1022 may include a temperature sensor (not shown in the figure) for sensing a temperature, but is not limited thereto. The thermal image device 102 is configured to generate the thermal image according to the temperature sensed by the sensor 1022. In addition, the thermal image device 102 may be utilized for generating a temperature array corresponding to the thermal image.

The thermal image device 102 may include a thermal image capturing device (not shown in the figure), wherein the thermal image capturing device may generate the thermal image and the corresponding temperature array according to the temperature sensed by the sensor, and each array element of the temperature array may correspond to each pixel of the thermal image. The processing device 104 is coupled to the thermal image device 102, and is configured to determine a region of interest ROI in the temperature array, determine a region of interest center reference point $P_{ROI}$ of the region of interest ROI, determine a plurality of corner points corresponding to the region of interest ROI, and determine the heat source location according to at least one of the corner points. For example, the processing device 104 may include a device having a computing unit for processing the temperature array and the thermal image generated from the thermal image device 102. In this way, the thermal image positioning system 10 according to an embodiment of the present invention may determine the corresponding region of interest ROI and the region of interest center reference point $P_{ROI}$ via the temperature array to precisely position a forehead location of a subject.

Figure 2:
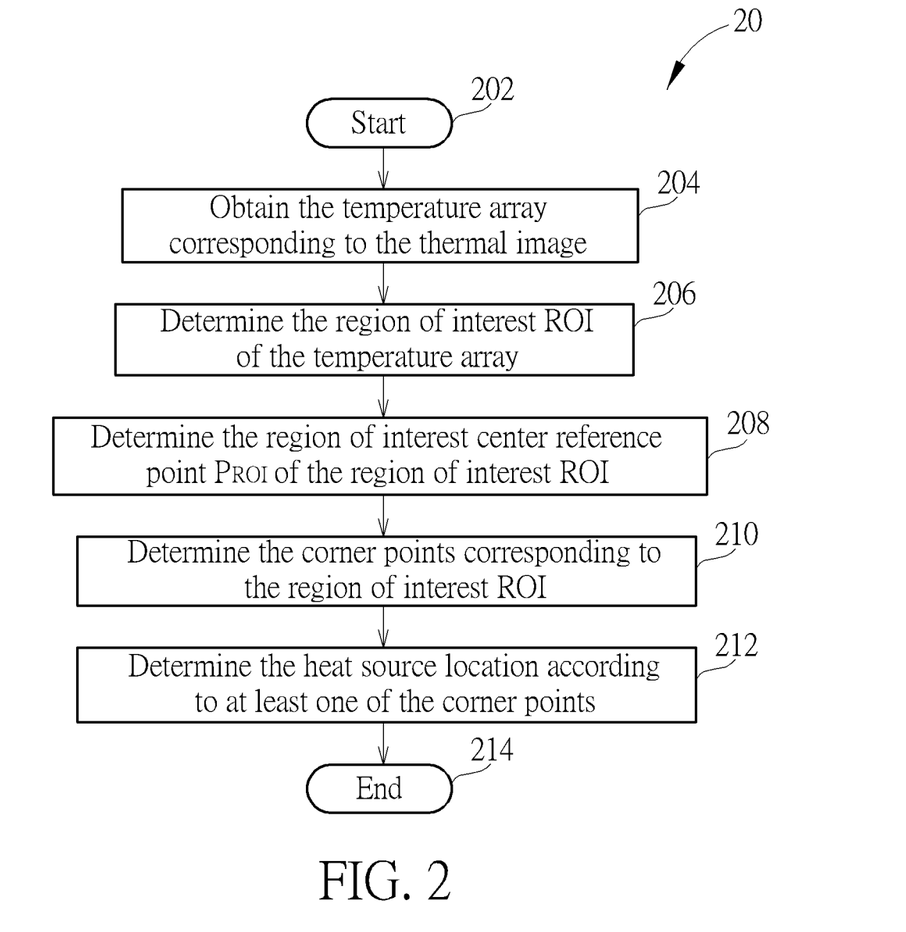
FIG. 2 is a schematic diagram of a thermal image positioning method according to an embodiment of the present invention.

In detail, refer to FIG. 2, which is a schematic diagram of a thermal image positioning method 20 according to an embodiment of the present invention. The thermal image positioning method 20 may be applied to the thermal image positioning system 10, and includes the following steps:

Step 202: Start;

Step 204: Obtain the temperature array corresponding to the thermal image;

Step 206: Determine the region of interest ROI of the temperature array;

Step 208: Determine the region of interest center reference point $P_{ROI}$ of the region of interest ROI;

Step 210: Determine the corner points corresponding to the region of interest ROI;

Step 212: Determine the heat source location according to at least one of the corner points;

Step 214: End.

Based on the thermal image positioning method 20, the thermal image device 102 is configured to obtain the thermal image information by the sensor 1022, and then the thermal image information is transmitted to the processing device 104 (step 204). In an embodiment, the thermal image information may be a temperature array of $M_T*M_T$, e.g. a temperature array of 80*80, but is not limited thereto.

In order to position the forehead location of the subject in the thermal image, in step 206, the processing device 104 may determine the region of interest ROI in the temperature array. Since an object having a higher temperature than a human body, e.g. a cup of coffee or hot drink, may be included in the thermal image, the accuracy of positioning the heat source location will be affected. Therefore, array elements in the temperature array higher than a temperature threshold T are filtered. More specifically, the temperature threshold T is a threshold to identify an array element with a highest temperature value; array elements adjacent to the array element having the highest temperature value are identified, and temperature values of all identified array elements are set as negative values such that the adjusted temperature values of the identified array elements are smaller than the temperature threshold T. The temperature array information is not affected, and the temperature array corresponding to the thermal image is obtained.

Figure 3A:
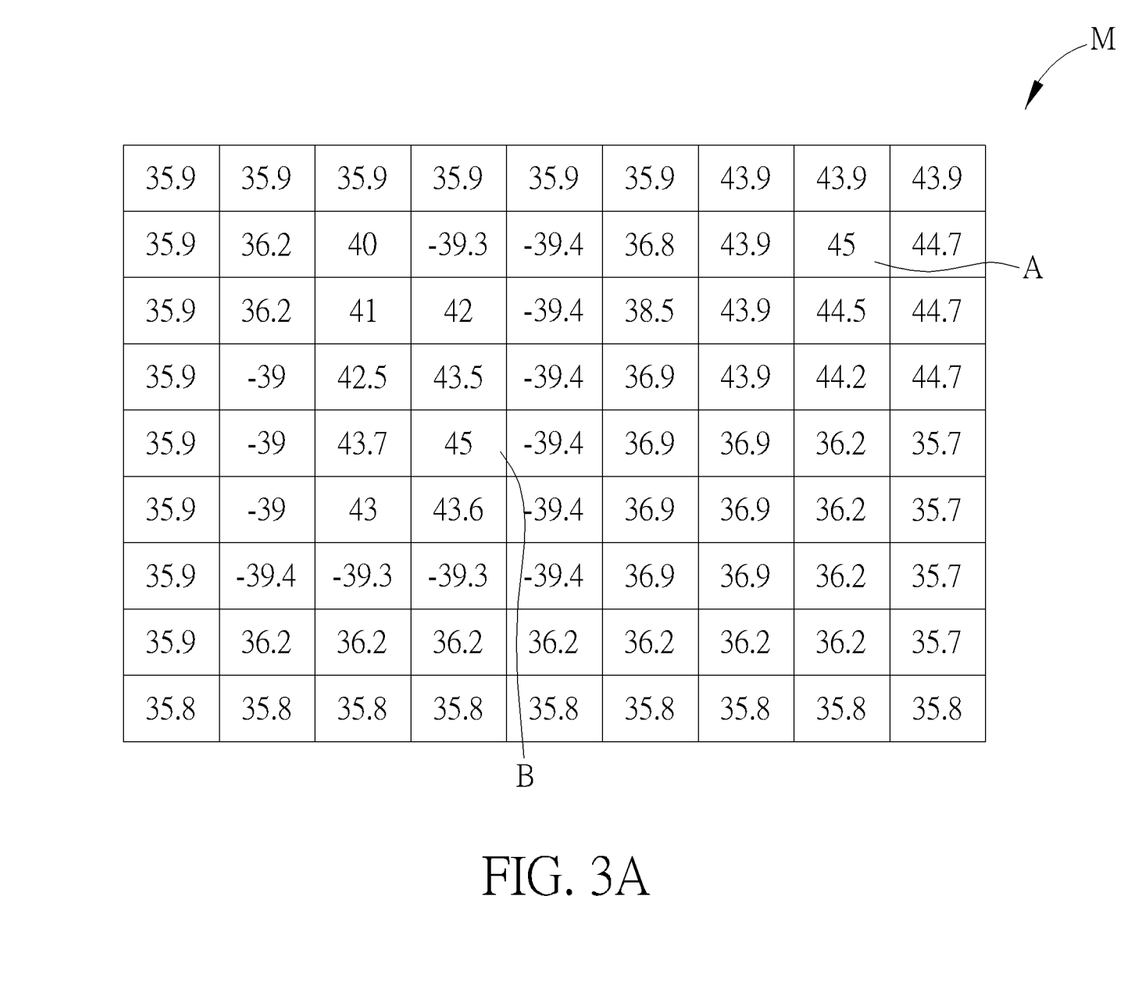
FIG. 3A is a schematic diagram of a temperature array according to an embodiment of the present invention.

More specifically, refer to FIG. 3A, which is a schematic diagram of a temperature array M according to an embodiment of the present invention. In FIG. 3A, an array mask of $N_T*N_T$ is utilized for determining an array element with a highest temperature value in the temperature array M, so as to identify other array elements higher than the temperature threshold T in the temperature array M. The temperature threshold T may be a value higher than an average temperature of a human body, e.g. higher than 42.5 degrees Celsius (° C.), but not limited thereto. This temperature is not within an average temperature interval of a human body. For example, the temperature value of an array element A and an array element B in FIG. 3A are both 45° C. and are determined not to be a subject. The array elements adjacent to the array elements A and B are identified in step 206. The corresponding values of the array elements A and B and the array elements around the array elements A and B are set as negative values to filter the array elements A and B and the array elements around the array elements A and B. After the values of the array elements A and B and the array elements adjacent to the array elements A and B are set as negative values, the temperature array M is adjusted to be free from including temperatures of non-subject matters.

Figure 3B:
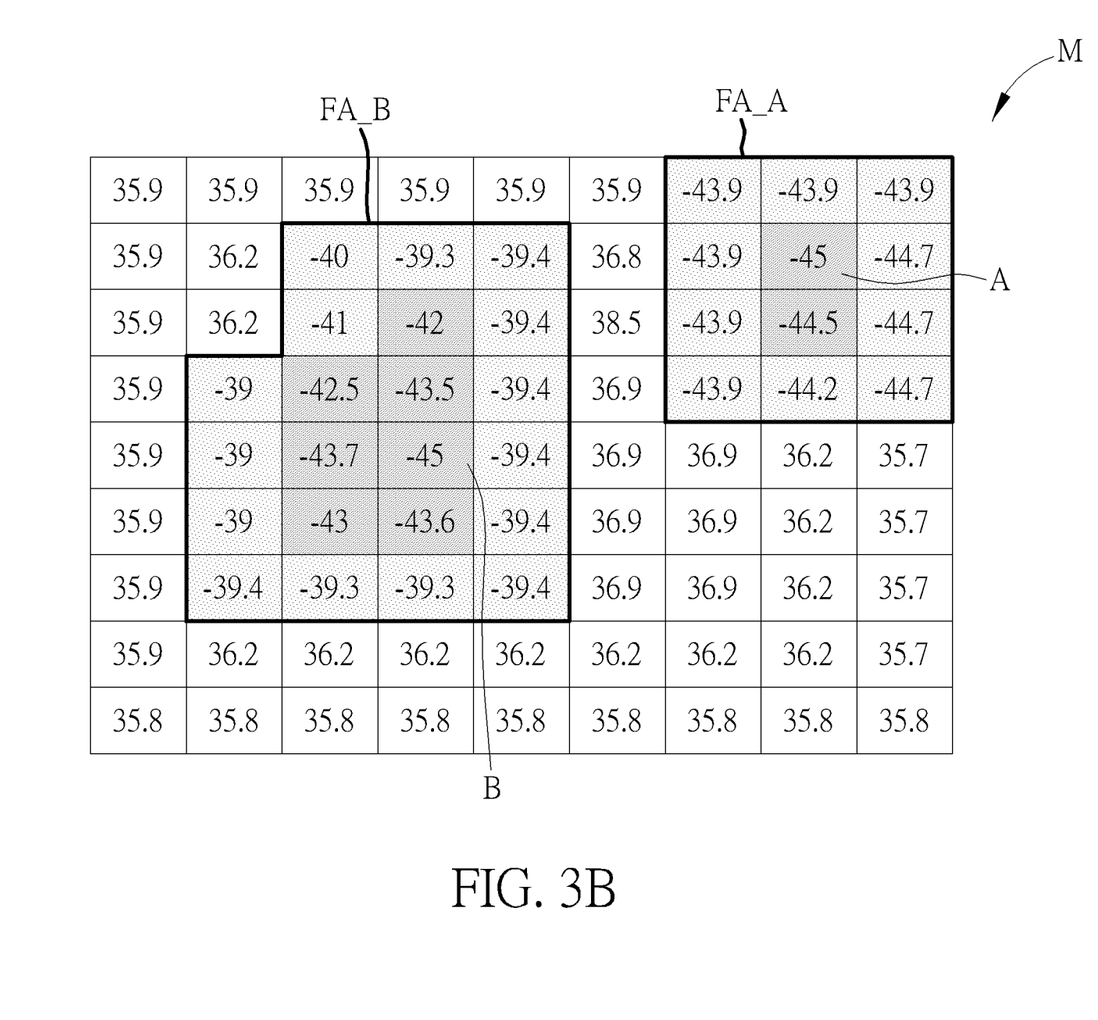
FIG. 3B is a schematic diagram of a regional broken temperature array according to an embodiment of the present invention.

Further, refer to FIG. 3B, which is a schematic diagram of a regional broken temperature array according to an embodiment of the present invention. In FIG. 3B, the values of the array elements A and B are adjusted from 45° C. to −45° C. and the array elements around the array elements A and B are adjusted to negative values in this step. In other words, the processing device 104 is configured to determine the array elements A and B having the highest temperature value. The processing device 104 is also configured to respectively determine the array elements A and B and the array elements adjacent to the array elements A and B with an array mask of 3*4 and an array mask of 4*6 in the temperature array M and identify the corresponding regional broken temperature arrays FA_A and FA_B. The regional broken temperature arrays FA_A and FA_B, for example, include the array elements A and B and their adjacent array elements, which have a temperature higher than the temperature threshold T.

Similarly, as shown in FIG. 3B, assuming that the temperature threshold T is set as 39° C., a value of the array elements and their adjacent array elements in the temperature array M higher than 39° C. are identified, and then the values of corresponding array elements are set as negative values to filter the array elements in the regional broken temperature arrays FA_A and FA_B. This avoids affecting data of the entire temperature array M. The regional broken temperature array FA_A and the regional broken temperature array FA_B are respectively a 3*4 array mask and a 4*6 array mask in the temperature array M shown in FIG. 3B. Notably, the values of the above embodiments are examples, and not limited thereto.

In order to determine a facial position of the human body in the region of the thermal image, the processing device 104 may further determine a high-temperature region HTZ according to the adjusted $M_T*M_T$ temperature array M in step 206, and determine a center point Pcenter, a highest temperature point Pmax, and an average temperature Tavg of the high-temperature region HTZ, wherein the center point Pcenter denotes a location of a center point of the high-temperature region HTZ, the highest temperature point Pmax denotes a location with a highest temperature of the high-temperature region HTZ, and the average temperature Tavg denotes an average value of all values in the high-temperature region HTZ. Therefore, the processing device 104 may determine the region of interest ROI with a $N_R*N_R$ array mask of the temperature array M according to the center point Pcenter, the highest temperature point Pmax, and the average temperature Tavg of the high-temperature region HTZ. Notably, the $N_R*N_R$ array mask is not required to be the same size as the high-temperature region HTZ.

Figure 4:
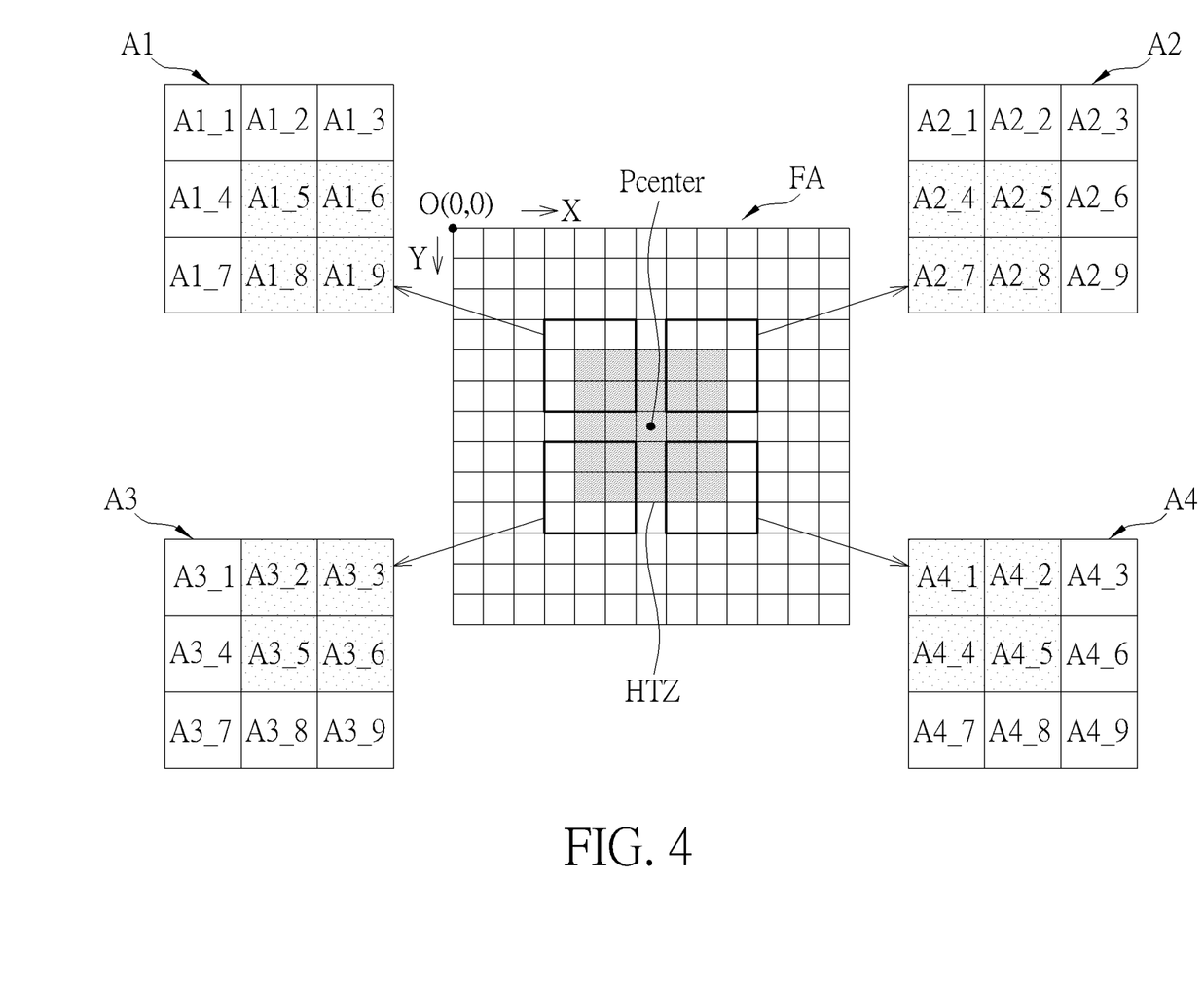
FIG. 4 is a schematic diagram of determining a region of interest according to an embodiment of the present invention.

More specifically, refer to FIG. 4, which is a schematic diagram of determining the region of interest ROI according to an embodiment of the present invention. In FIG. 4, assume an origin coordinate 0 (0, 0) in the thermal image, wherein values of X-axis are increased from left to right and values of Y-axis are increased from top to bottom. The $N_R*N_R$ array mask may be a 7*7 array mask for determining the high-temperature region HTZ in the temperature array M corresponding to the thermal image, and determining the center point Pcenter, the highest temperature point Pmax, and the average temperature Tavg in the high-temperature region HTZ. For example, the high-temperature region HTZ in FIG. 4 may be a 5*5 array mask, but not limited thereto; the $N_R*N_R$ array mask may be larger than the high-temperature region HTZ.

In an embodiment, in step 208, the processing device 104 is configured to determine a nearest region, which is of the center point Pcenter of the high-temperature region HTZ toward four corners of the $N_R*N_R$ array mask, according to an Ns*Ns array mask. In step 210, the corner points of the nearest region corresponding to the four corners of the $N_R*N_R$ array mask are respectively determined. For example, in an embodiment of FIG. 4, the Ns*Ns array mask may be a 3*3 array mask, and the nearest regions A1-A4 are respectively determined based on the center point Pcenter toward the four corners of the 7*7 array mask. Notably, the $N_R*N_R$ array mask is larger than the Ns*Ns array mask; the above embodiments are for examples, and not limited thereto.

Taking the nearest region A1 as an example, the nearest region A1 includes the array elements A1_1-A1_9, and the processing device 104 is configured to respectively compare values of the array elements A1_1-A1_9 with the average temperature Tavg. When a comparison result is that the values of the array elements A1_5, A1_6, A1_8, A1_9 are higher than the average temperature Tavg, the array elements A1_5, A1_6, A1_8, A1_9 belong to an inner angle region, the array elements A1_1-4, A1_7 belong to an external angle region, and a corner point P1 is determined in the nearest region A1. Similarly, the array elements A2_4, A2_5, A2_7, A2_8 of the nearest region A2 belong to the inner angle region, the array elements A2_1-3, A2_6, A2_9 of the nearest region A2 belong to the external angle region, a corner point P2 is determined in the nearest region A2 and so forth, until a corner point P3 is determined in the nearest region A3 and a corner point P4 is determined in the nearest region A4.

Furthermore, the processing device 104 may take the corner point P1 as a reference point and determine the region of interest center reference point $P_{ROI}$ according to a top side length Wtop and a side length H, wherein the top side length Wtop is determined by the corner points P1, P2, and the side length H is determined by the corner points P1, P3 or P2, P4. For example, the side length H may be a left side length Hleft formed by the corner points P1, P3. When a coordinate of the corner point P1 is (P1_x, P1_y), a coordinate of the region of interest center reference point $P_{ROI}$ is (P1_x+Wtop/2, P1_y+Hleft/2). In other words, the side length H may be a right side length Hright formed by the corner points P2, P4. When a coordinate of the corner point P2 is (P2_x, P2_y), a coordinate of the region of interest center reference point $P_{ROI}$ is (P2_x+Wtop/2, P2_y+Hright/2).

Since a hottest point of the upper part of a human body may be located at the forehead, nose, mouth or neck of a human face, i.e. a hottest point in the thermal image may be approximately located around a vertical line of the human face, the location of the highest temperature point Pmax determined by the processing device 104 is located at or around one of the above hottest points.

Figure 5:
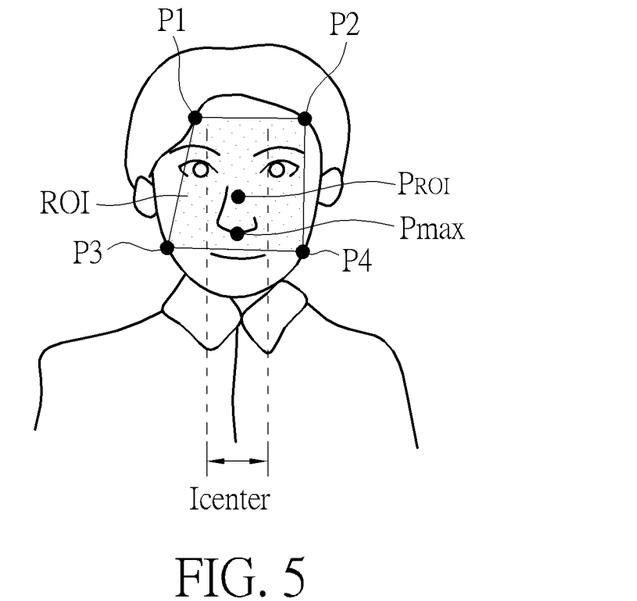
FIG. 5 and FIG. 6 are schematic diagrams of a relation between corner points of the region of interest and a human face according to an embodiment of the present invention.

Refer to FIG. 5, which is a schematic diagram of a relation between corner points P1-P4 of the region of interest ROI and a human face according to an embodiment of the present invention. The thermal image positioning method 20 according to an embodiment of the present invention firstly determines the region of interest ROI (i.e. a head position of the human body) of the high-temperature region HTZ from the temperature array M of the thermal image, and then the processing device 104 may determine the heat source location according to at least one of the corner points P1-P4 of the region of interest ROI in step 212.

In FIG. 5, the processing device 104 may define a center point interval Icenter to determine whether the region of interest center reference point $P_{ROI}$ is located inside the center point interval Icenter for determining whether the region of interest ROI (i.e. the head position of the human body) is correctly determined. When the region of interest center reference point $P_{ROI}$ is located inside the center point interval Icenter, the processing device 104 is configured to determine the heat source location according to at least one of the corner points of the $N_R*N_R$ array mask. Notably, the center point interval Icenter is generated according to the highest temperature point Pmax of the high-temperature region HTZ and the $N_R*N_R$ array mask. For example, the center point interval Icenter may be a multiple of a length NR of the $N_R*N_R$ array mask (e.g. 1*$N_R$, 2*$N_R$, 3*$N_R$), and the length NR is approximately smaller than a facial width of the human body, but not limited thereto.

With regards to determining the heat source location according to at least one of the corner points of the $N_R*N_R$ array mask, in an embodiment, assuming the center point interval Icenter is l*$N_R$ and the region of interest ROI is the head position of the human body, the heat source location $P_{source}$ (i.e. the forehead location) is determined by the corner points P1, P2 and a formula (1).

$$P_{source}(x,y)=(Pn\_x, Pn\_y+1), n=1,2 (\text{if } P1\_y > P2\_y, \quad n=1, \text{else } n=2) \quad (1)$$

The formula (1) is utilized for determining whether the region of interest center reference point $P_{ROI}$ is located inside the center point interval Icenter, where the highest temperature point Pmax is located. As such, when a difference between an X-axis coordinate value of the region of interest center reference point $P_{ROI}$ and an X-axis coordinate value of the highest temperature point Pmax is smaller than $\frac{1}{2}*N_R$ (i.e. smaller than $\frac{1}{2}*N_R$ pixels), the heat source location $P_{source}$ (x, y)=(Pn_x, Pn_y+1). Notably, the formula (1) is utilized for determining a Y-axis coordinate value of the corner points P1, P2, and the corner point with larger Y-axis coordinate value is determined as the heat source location (i.e. closer to the upper thermal image). In addition, since the forehead location is usually located below the corner point in practice, the Y-axis coordinate value of the heat source location $P_{source}$(x, y) is increased by 1, which shifts the lower side of the thermal image, wherein the shift value is not limited to 1.

Figure 6:
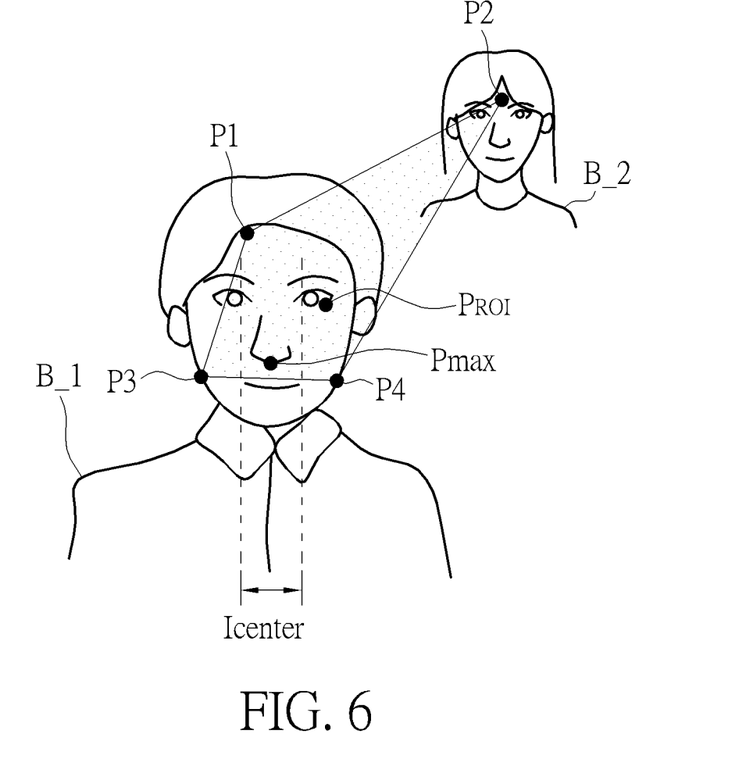

In an embodiment, when any part of the region of interest ROI is deformed or shifted, a correspondence between the corner points P1-P4 of the region of interest ROI and the face of the human body is shown in FIG. 6. In FIG. 6, the corner points P1, P3, P4 are located at a human body B_1, and the corner point P2 is located at a human body B_2, i.e. the corner point P2 is positioned on a human body different from that of corner points P1, P3 and P4. In this situation, since the region of interest center reference point $P_{ROI}$ does not satisfy the condition of the formula (1), the processing device 104 is required to further determine the heat source location $P_{source}$ (i.e. the forehead location) according to the corner points P1, P2 and a formula (2) or a formula (3).

$$(|P_{ROI}\_x - P\max\_x| > \tfrac{1}{2}*N_R) \& (|P1\_x - P\max\_x| < \tfrac{1}{2}*N_R) \rightarrow P_{source}(x,y)=(P1\_x, P1\_y+1) \quad (2)$$

$$(|P_{ROI}\_x - P\max\_x| > \tfrac{1}{2}*N_R) \& (|P2\_x - P\max\_x| < \tfrac{1}{2}*N_R) \rightarrow P_{source}(x,y)=(P2\_x, P2\_y+1) \quad (3)$$

The formulas (2), (3) are utilized for determining whether a difference between the X-axis coordinate value of the corner point P1 or the corner point P2 and the highest temperature point Pmax is smaller than $\frac{1}{2}*N_R$ (i.e. smaller than $\frac{1}{2}*N_R$ pixels). More specifically, the formula (2) is true when the difference between the X-axis coordinate value of the corner point P1 and the x-axis coordinate value of the highest temperature point Pmax is smaller than $\frac{1}{2}*N_R$, the heat source location $P_{source}$=(P1_x, P1_y+1). The formula (3) is true when the difference between the X-axis coordinate value of the corner point P2 and the X-axis coordinate value of the highest temperature point Pmax is smaller than ½*$N_R$, the heat source location $P_{source}$=(P2_x, P2_y+1).

In another situation, when the corner points P1, P2 are both located outside the center point interval Icenter, i.e. the corner points P1, P2 do not satisfy the formulas (2), (3), the processing device 104 takes the highest temperature point Pmax of the high-temperature region HTZ as the heat source location $P_{source}$.

Therefore, the thermal image positioning method 20 according to an embodiment of the present invention may avoid identifying non-human objects and prevent interference from other human bodies when determining the temperature of a specific human body to precisely position the forehead location of the human body.

Figure 7:
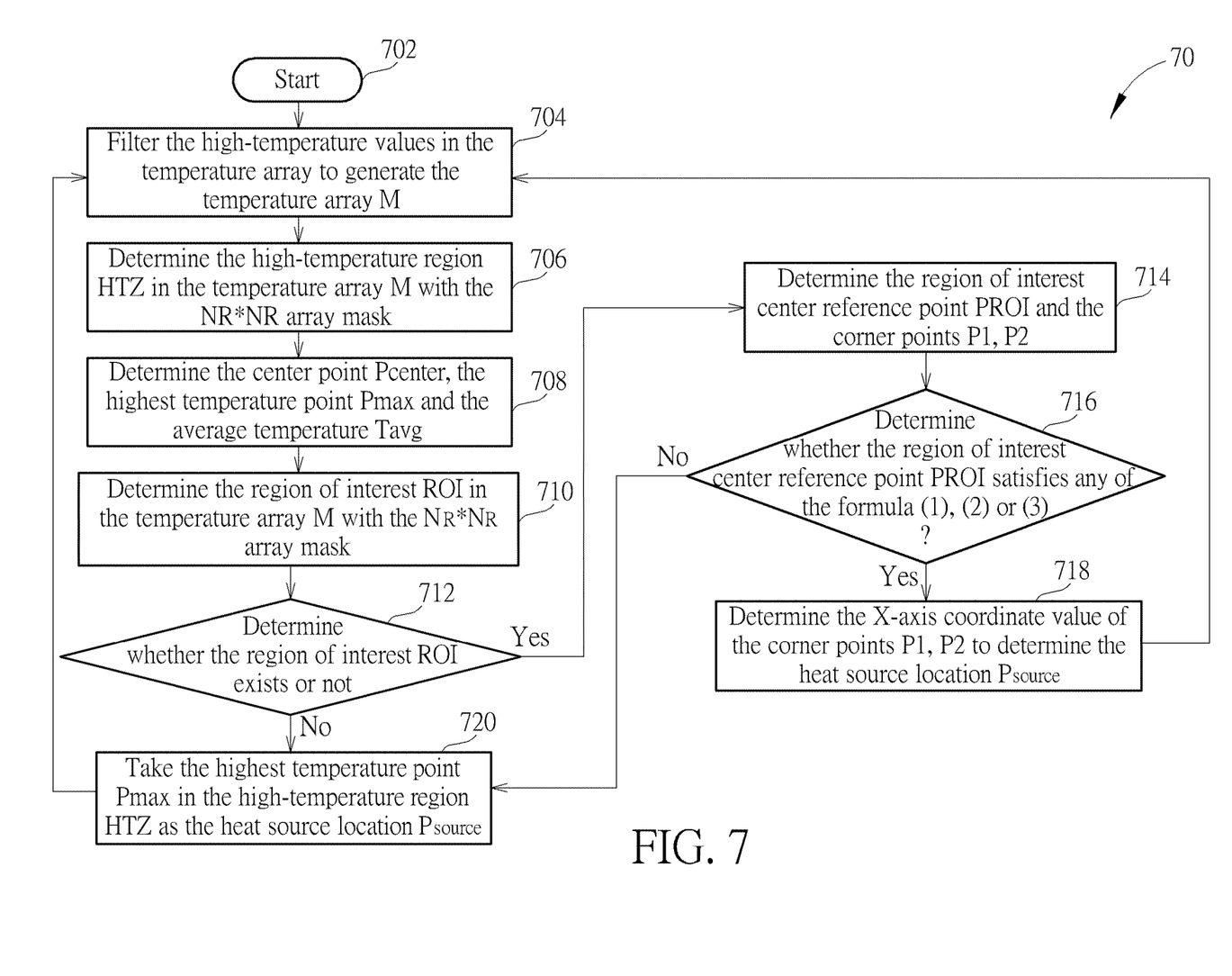
FIG. 7 is a schematic diagram of a thermal image positioning method according to an embodiment of the present invention.

An operation process of the above thermal image positioning system 10 may be concluded to a thermal image positioning method 70. After the thermal image positioning system 10 obtains the temperature array of the thermal image, the forehead location of the human body and corresponding temperature may be determined according to the thermal image positioning method 70. The thermal image positioning method 70 includes the following steps:

Step 702: Start;
Step 704: Filter the high-temperature values in the temperature array to generate the temperature array M;
Step 706: Determine the high-temperature region HTZ in the temperature array M with the $N_R$*$N_R$ array mask;
Step 708: Determine the center point Pcenter, the highest temperature point Pmax and the average temperature Tavg;
Step 710: Determine the region of interest ROI in the temperature array M with the $N_R$*$N_R$ array mask;
Step 712: Determine whether the region of interest ROI exists or not. If yes, go to step 714; if no, go to step 720;
Step 714: Determine the region of interest center reference point $P_{ROI}$ and the corner points P1, P2;
Step 716: Determine whether the region of interest center reference point $P_{ROI}$ satisfies any of the formula (1), (2) or (3). If yes, go to step 718; if no, go to step 720;
Step 718: Determine the X-axis coordinate value of the corner points P1, P2 to determine the heat source location $P_{source}$;
Step 720: Take the highest temperature point Pmax in the high-temperature region HTZ as the heat source location $P_{source}$.

The operation process of the thermal image positioning method 70 may be known by referring to the above embodiments of the thermal image positioning system 10 and the thermal image positioning method 20 and are not narrated herein for brevity.

Notably, the embodiments of the present invention illustrated above may be properly modified by those skilled in the art, and are not limited thereto. For example, sizes of the $N_T$*$N_T$ array mask for filtering the high-temperature values in the temperature array, the $N_R$*$N_R$ array mask for determining the region of interest ROI or the array mask for determining the nearest region, a ratio of the thermal image size, amounts and methods to determine the corner points, and a range of the center point interval Icenter may all be adjusted according to requirements of a user and computer system, and directions in the figures are defined for better illustrating the embodiments and not limited thereto.

In summary, the present invention provides a thermal image positioning method and a thermal image positioning system to determine a head position and a highest temperature location of a human body by a temperature array corresponding to a thermal image to precisely position a forehead location of the human body.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A thermal image positioning method, for determining a heat source location of the thermal image, comprising:
   obtaining a temperature array corresponding to the thermal image;
   determining a region of interest (ROI) of the temperature array;
   determining an ROI center reference point of the ROI;
   determining a plurality of corner points corresponding to the ROI; and
   determining the heat source location according to at least one of the plurality of corner points.

2. The thermal image positioning method of claim 1, further comprising:
   filtering a high-temperature value to generate the temperature array;
   determining a high-temperature region in the temperature array;
   determining a center point, a highest temperature point, and an average temperature of the high-temperature region; and
   determining the region of interest in the high-temperature region with a first array mask according to the center point, the highest temperature point, and the average temperature of the high-temperature region.

3. The thermal image positioning method of claim 2, wherein the step of filtering the high-temperature value to generate the temperature array comprises:
   determining an array element higher than a temperature threshold;
   determining the array element and array elements adjacent to the array element with a second array mask; and
   filtering a value of the array element and values of the array elements adjacent to the array element;
   wherein the temperature threshold is higher than an average temperature of a human body.

4. The thermal image positioning method of claim 2, further comprising:
   determining a nearest region defined by the center point of the high-temperature region toward four corners of the first array mask according to a third array mask; and
   respectively determining corner points of the nearest region corresponding to the four corners of the first array mask.

5. The thermal image positioning method of claim 4, wherein the first array mask is larger than the third array mask.

6. The thermal image positioning method of claim 4, wherein the step of determining the heat source location according to at least one of the plurality of corner points comprises:
   determining that the ROI center reference point is located in a center point interval;
   determining the heat source location according to at least one of the corner points of the first array mask;
   wherein the center point interval is determined according to the highest temperature point of the high-temperature region and the first array mask.

7. The thermal image positioning method of claim 6, wherein the step of determining the heat source location according to at least one of the plurality of corner points comprises:

respectively determining a first corner point and a second corner point are located in the center point interval according to the first corner point and the second corner point of the corner points corresponding to the four corners of the first array mask so as to determine the heat source location.

8. The thermal image positioning method of claim 7, wherein when both of the first corner point and the second corner point are determined to be outside the center point interval, the highest temperature point of the high-temperature region is determined as the heat source location.

9. The thermal image positioning method of claim 5, wherein the ROI center reference point is determined according to a top side length and a side length of a rectangle formed by the corner points corresponding to the four corners of the first array mask.

10. A thermal image positioning system, for determining a heat source location of a thermal image, comprising:

a thermal image device, configured to generate a temperature array corresponding to the thermal image; and a processing device, coupled to the thermal image device, configured to determine a region of interest (ROI) of the temperature array, determine an ROI center reference point of the ROI, determine a plurality of corner points corresponding to the ROI, and determine the heat source location according to at least one of the plurality of corner points.

11. The thermal image positioning system of claim 10, wherein the processing device is configured to filter a high-temperature value to generate the temperature array, determine a high-temperature region in the temperature array, determine a center point, a highest temperature point, and an average temperature of the high-temperature region, and determine the region of interest in the high-temperature region with a first array mask according to the center point, the highest temperature point, and the average temperature of the high-temperature region.

12. The thermal image positioning system of claim 11, wherein the processing device is configured to determine an array element higher than a temperature threshold, determine the array element and array elements adjacent to the array element with a second array mask, and filter a value of the array element and values of the array elements adjacent to the array element, wherein the temperature threshold is higher than an average temperature of a human body.

13. The thermal image positioning system of claim 11, wherein the processing device is configured to determine a nearest region defined by the center point of the high-temperature region toward four corners of the first array mask according to a third array mask, and respectively determine corner points of the nearest region corresponding to the four corners of the first array mask.

14. The thermal image positioning system of claim 13, wherein the first array mask is larger than the third array mask.

15. The thermal image positioning system of claim 13, wherein the processing device is configured to determine the ROI center reference point is located in a center point interval according to at least one of the corner points of the first array mask so as to determine the heat source location, wherein the center point interval is determined according to the highest temperature point of the high-temperature region and the first array mask.

16. The thermal image positioning system of claim 15, wherein the processing device is configured to respectively determine a first corner point and a second corner point are located in the center point interval according to the first corner point and the second corner point of the corner points corresponding to the four corners of the first array mask so as to determine the heat source location.

17. The thermal image positioning system of claim 16, wherein the processing device is configured to determine the highest temperature point of the high-temperature region as the heat source location when both of the first corner point and the second corner point are determined to be outside the center point interval.

18. The thermal image positioning system of claim 14, wherein the ROI center reference point is determined according to a top side length and a side length of a rectangle formed by the corner points corresponding to the four corners of the first array mask.

19. The thermal image positioning system of claim 10, wherein the thermal image device comprises a sensor configured to sense a temperature, and the thermal image device is configured to generate the thermal image according to the temperature sensed by the sensor.

* * * * *